United States Patent
Palumbo

[11] Patent Number: 6,106,925
[45] Date of Patent: Aug. 22, 2000

[54] COVERSHEET FOR AN ABSORBENT PRODUCT

[75] Inventor: Gianfranco Palumbo, Bad Homburg, Germany

[73] Assignee: The Procter & Gamble Company, Cincinnati, Ohio

[21] Appl. No.: 09/253,252

[22] Filed: Feb. 19, 1999

Related U.S. Application Data

[63] Continuation of application No. 08/817,314, filed as application No. PCT/US95/13028, Oct. 5, 1995, abandoned.

[30] Foreign Application Priority Data

Oct. 7, 1994 [IT] Italy .................................. TO94A0799

[51] Int. Cl.[7] ....................................................... B32B 3/24
[52] U.S. Cl. ...................... 428/137; 428/138; 428/296.7; 428/295.1; 604/378; 604/383; 442/398; 442/399; 442/409
[58] Field of Search .................................. 428/137, 138, 428/296.7, 295.1; 604/378, 383; 442/398, 399, 409

[56] References Cited

U.S. PATENT DOCUMENTS

| | | | |
|---|---|---|---|
| 3,649,431 | 3/1972 | Parker | 428/137 |
| 4,525,407 | 6/1985 | Ness | 428/138 |
| 4,657,802 | 4/1987 | Morman | 428/152 |
| 5,037,416 | 8/1991 | Allen et al. | 604/385.1 |
| 5,188,625 | 2/1993 | Van Item et al. | 604/383 |
| 5,567,501 | 10/1996 | Srinivasan et al. | 428/137 |
| 5,628,097 | 5/1997 | Benson et al. | 28/165 |
| 5,830,555 | 11/1998 | Srinivasan et al. | 428/137 |

*Primary Examiner*—William P. Watkins, III
*Attorney, Agent, or Firm*—Kevin D. Hogg; Steven W. Miller; Jacobus C. Rasser

[57] ABSTRACT

A coversheet is provided for covering an absorbent body of an absorbent sanitary article. The coversheet is elastic in at least one direction and has perforations which extend therethrough. The coversheet has an upper layer including a nonwoven material intended to face outwardly of the absorbent body, an intermediate layer including an elastic film, and a lower layer including a nonwoven material intended to face towards the absorbent body. The upper and lower layers are connected to the intermediate layer only around the perimeters of the perforations.

21 Claims, 6 Drawing Sheets

COVERSHEET FOR AN ABSORBENT PRODUCT

This is a continuation of application Ser. No. 08/817,314 filed on Feb. 4, 1998 and now abandoned, which is 35 U.S.C. §371 of PCT/US95/13028 filed on Oct. 5, 1995.

FIELD OF THE INVENTION

This invention relates to a coversheet for an absorbent product, more particularly for sanitary products, such as sanitary towels, diapers, and sanitary pads for adults. Such products, which are intended to absorb and retain body fluids such as menstrual fluids, urine and blood, are in common use as disposable products, that it is to say, products intended to be thrown away after use.

BACKGROUND OF THE INVENTION

Such products typically comprise an absorbent core of porous material which can absorb and retain a large quantity of fluid. The core can be regarded as having a top face intended to face the body of the user, and a back face intended to face the external environment. The absorbent core almost always has a sheet which covers the top face, and is referred conventionally and herein as a topsheet, and generally, though not always, it has a further coversheet which covers the back face and is referred to conventionally and herein as a backsheet. The topsheet must be fluid-permeable, to allow body fluids to pass therethrough into the absorbent core. For this purpose it is known, for example to provide perforations in the topsheet. The present invention is concerned with a novel form of topsheet.

Until recent years, all, or at least substantially all, absorbent products for sanitary use were substantially or wholly inelastic. However, in more recent times it has been appreciated that it would be advantageous for at least some types of absorbent sanitary product to be elastic. Our copending application entitled "Absorbent Sanitary Article", application TO94A000797 IT, filed on the same date as the present application, describes one such absorbent product, the preferred embodiments of which are in the form of pantiliners.

One of the problems which can arise in constructing such an absorbent product is in the provision of a suitable topsheet. At least in some forms of elastic absorbent product the topsheet itself may need to be elastic, and it is believed that at present no suitable elastic topsheets are available. It is an object of the present invention to remedy this.

In EP-A-207904 there is described a covering sheet for covering an absorbent body of an absorbent sanitary article, the said structure having perforations which extend therethrough and comprising an upper layer intended to face outwardly of the absorbent body and comprising a non-woven fibrous material, an intermediate layer comprising a film, and a lower layer intended to face inwardly towards the absorbent body and comprising a non-woven fibrous material. It has been found that an elastic topsheet can be made following a modified form of the teachings of EP-A-207904, replacing the intermediate layer used therein with an elastic film. This is surprising, since the process for joining the three layers together would have been expected, prima facie, to result in the elastic film no longer being able to exhibit its elastic properties, as a result of its connection on both sides to the fibrous layers. However, it has been found the process described in EP-A-207904 can be modified so that it does not in fact have this effect. The modification has the effect that the upper and lower layers are connected to the intermediate layer substantially only around the perimeters of the perforations, and this permits the elastic film to continue to exhibit its elasticity in at least one direction.

SUMMARY OF THE INVENTION

Thus, according to the present invention there is provided a covering structure for covering an absorbent body of an absorbent sanitary article, the said structure having perforations which extend therethrough and being elastic in at least one direction, the structure comprising:

(a) an upper layer intended to face outwardly of the absorbent body and comprising a non-woven fibrous material;

(b) an intermediate layer comprising an elastic film; and (c) a lower layer intended to face inwardly towards the absorbent body and comprising a non-woven fibrous material; the upper and lower layers being connected to the intermediate layer substantially only around the perimeters of the perforations.

The upper and lower layers may be formed of non-woven webs in which the individual fibres are aligned with one another to a substantial extent. Where that is so, the topsheet will be elastic in a direction transverse to the direction of alignment of the fibres, but substantially inelastic in a direction parallel to the direction of alignment. It follows from this that one cannot have the upper and lower layers with directions of alignment which are perpendicular to one another, since then the resulting topsheet would be substantially inelastic. On the contrary, one would normally have the directions of alignment the same in the upper and lower layers. If the fibres in either or both of the upper and lower layers are randomly oriented there will be some elasticity in all directions, but much less than the elasticity obtained when the fibres are oriented. It will be appreciated that there are intermediate possibilities between the two extremes of complete orientation and complete randomness, and that these will give intermediate amounts of elasticity and greater or lesser differences between the amount of elasticity in different directions.

The materials used for the upper and lower layers can be the same as those described in EP-A-207904, though they need not be. Thus, for example, both layers may be made of carded fibres, and these may be, for example, polypropylene fibres or two-component fibres sold under the name CHISSO ES by the Japanese company Chisso. The upper and lower layers may be hydrophobic, hydrophilic, or have at least one region which is hydrophobic and at least one region which is hydrophilic.

The material used for the elastic film is preferably based on a thermoplastic elastomer, and suitable materials include styrenic block copolymers (such as styrene-butadiene-styrene, styrene-isoprene-styrene, styrene-ethylene butylene-styrene and styrene-ethylene propylene-styrene copolymers), elastomeric polyurethanes, polyester and polyether elastomers and copolymers thereof, polyester-amides, poly-ether-ester amides and ionomers (polymeric materials in which chains are linked by ionic interactions). Other suitable materials include blends of or a polyolefin material (such as polypropylene, polyethylene, and copolymers thereof, in particular polyethylene vinyl acetate) with a rubber such as EPR or SBR rubber.

The film preferably has a thickness of from 8 to 100 $\mu$m, more preferably not more than 70 $\mu$m, and still more preferably from 30 $\mu$m to 50 $\mu$m. However, a still thinner film, having a thickness of, say 15–30 $\mu$m may be desirable. One particular film which can be used is that sold by the Exxon Chemical Corporation as EXX 500. This is available in a thickness of 50 µm. These values refer to the true thickness of the film. If an embossed film in used it may have a much greater apparent thickness, say 500 µm, including the embossings.

BRIEF DESCRIPTION OF THE DRAWINGS

Referring now to the accompanying drawings.

DETAILED DESCRIPTION OF THE INVENTION

Figure 1:
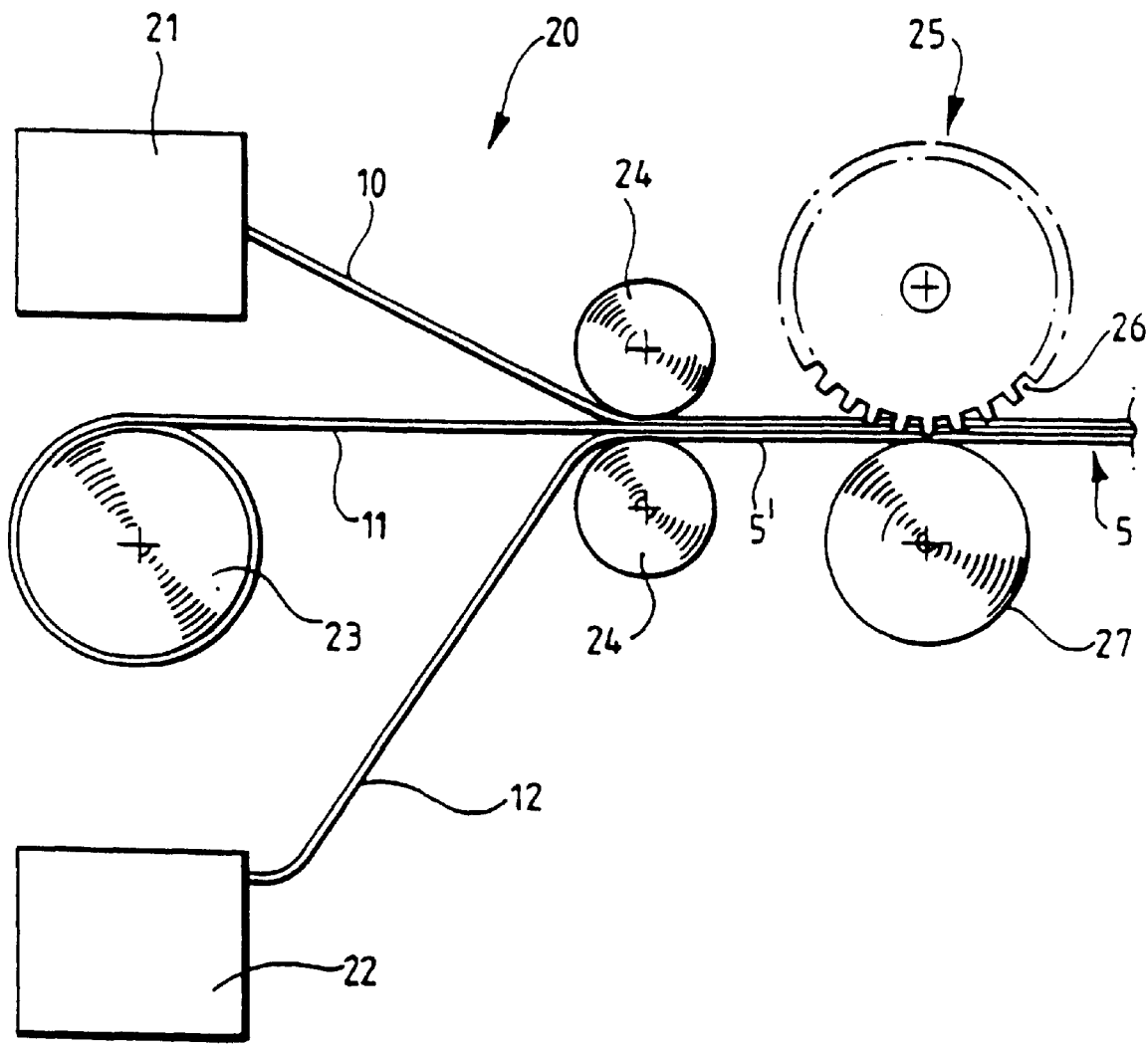
FIG. 1 illustrates diagrammatically a method of manufacturing a topsheet according to the present invention.

Referring in more detail to FIG. 1, this shows schematically a device generally indicated 20, which comprises two cards 21, 22 each of which continuously supplies a web of polypropylene or other suitable fibres. The web supplied by the card 21 forms an upper layer 10 and the web supplied by the card 22 forms the lower layer 12.

An elastic film intended to constitute an intermediate layer 11, is unwound continuously from a reel, generally indicated 23.

The webs 10 and 12 and the film 11 are fed towards two guide rollers 24 in a disposition such that the film 11 is interposed between the webs 10 and 12. The resulting assembly 5' is then directed to a perforating and bonding station, generally indicated 25, constituted by two counter-rotating superposed rollers 26, 27 with parallel axes. The lower roller 27, which acts as a rotary support for the assembly 5', has a generally smooth surface. The upper roller 26, however, has teeth or projections arranged in an array corresponding to that of the perforations which it is wished to make in the eventual product 5. At least the roller 26 is heated to a temperature sufficient to cause partial melting of those fibres of the web 10 into which it comes into contact.

The teeth or projections of the roller 26 penetrate the strip 5. This serves simultaneously to form the above mentioned perforations in the strip, and to effect thermal bonding of the film 11 to the webs 10 and 12. This takes place by virtue of the fact that fibres from web 10 are forced into the perforations, where they are bonded to the film 11 and, in some cases, to the web 12. Also material from the film 11 is forced into the web 12 and thermally bonded thereto. The bonding is a result partly of the heat from the teeth, and partly from the pressure which they apply. Bonding between the film 11 and the webs 10 and 12 the takes place only at the edges of the perforations. The effect of this limited bonding is that the elastic film is able to continue to manifest its elasticity is a direction transverse to the orientation of the fibres of the web 10. This means that, as already mentioned, the eventual product has maximum elasticity when the fibres in the web 10 are all aligned with one another, the fibres in the web 12 are all aligned with one another, and the fibres in web 10 are aligned with those in web 12.

Figure 5:
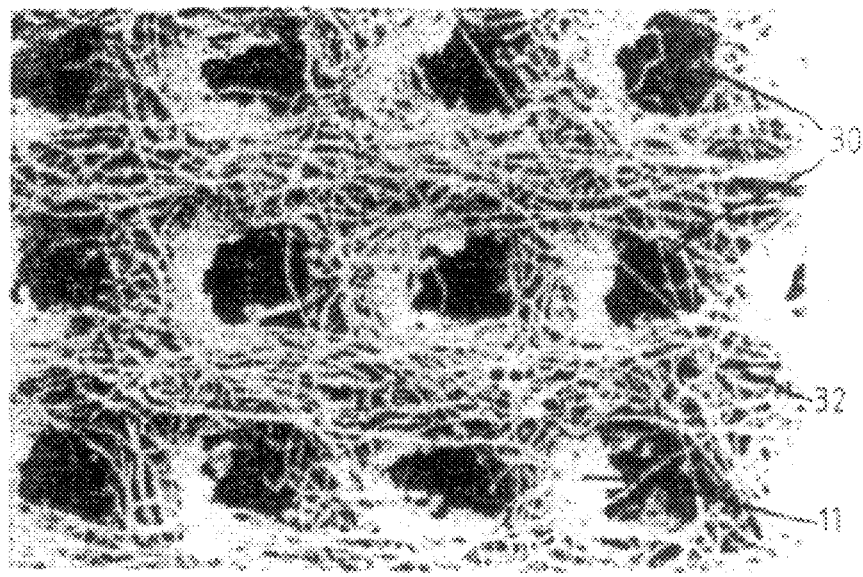
FIG. 5 is a photomicrograph showing a material according to the invention, from below.
Figure 6:
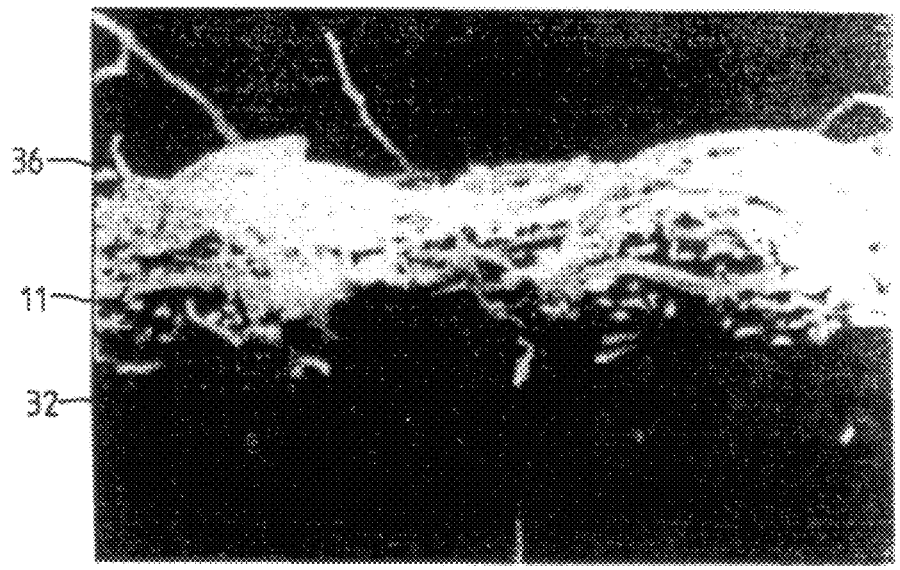
FIG. 6 is a photomicrograph, on a larger scale, showing a transverse section through the material of FIG. 5.
Figure 7:
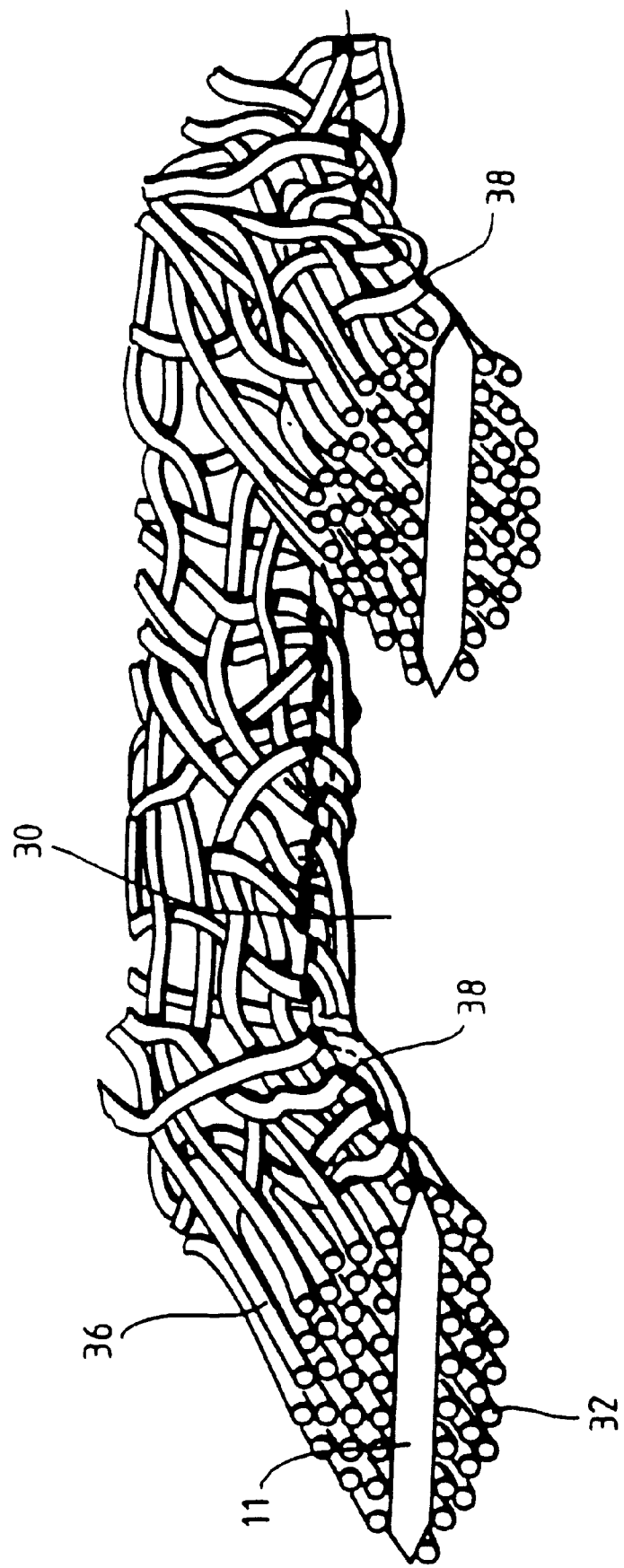
FIG. 7 is a perspective, diagrammatic view showing substantially what appears in FIG. 6.

Further details of the structure according to the invention can be seen in FIGS. 5, 6 and 7. FIG. 5 shows a square array of perforations 30 and fibres 32 of the lower fibrous layer. Also visible in FIG. 5, around the perimeter of each of the perforations 30, are portions of the intermediate elastic film 11, which have been forced into the perforations in the course of manufacturing the structure. The transverse section of FIG. 6, which is taken along a line passing through one of the perforations 30, shows the fibres 32, the film 11, and fibres 36 of the upper fibrous layer. FIG. 7 shows substantially what is in FIG. 6, but in a simplified, diagrammatic form. Reference numeral 38 indicates the area around the perimeter of each of the perforations 30 where the fibrous layers and elastic film are bonded together.

The size and spacing of the above mentioned perforations can be chosen according to the intended use of the product. However, it has been found appropriate to have the perforations arranged in a square array with approximately 7 perforations per linear cm in each direction (i.e. 49 perforations per $cm^2$), with each perforation being square and having a side length of about 0.7 mm. However, it must be emphasised that other arrangements and sizes of perforations can be employed. Some are described in EP-A-207904, referred to above, to which attention is directed for details.

One embodiment of the topsheet according to the invention will now be identified in more detail by way of example. This comprises upper and lower webs 10 and 12 respectively, both made of polypropylene carded fibres of 1.7 dtex. The upper web has a basis weight which is higher than the basis weight of the lower web in a ratio of 1.2:1, with the combined basis weights of the two webs being 30 $g/m^2$. The film 11 is a thermoplastic, elastomeric, styrenic block copolymer based film, 40 µm thick and with a basis weight of about 35 $g/m^2$, available from Exxon Chemical Corporation under the name EXX 500. The overall basis weight of the material is therefore approximately 65 $g/m^2$. Perforations are formed therein in a square array, with the sides of each perforation having a length of approximately 0.7 mm, and with the spacing between the centres of adjacent perforations being approximately 1.4 mm.

It will be understood that various modifications may be made to the embodiment just described. For example, the webs 10 and 12 may be made of fibres having some other diameter (as an example, 2.2 dtex fibres have also been used and found to be acceptable, though the results given by the 1.7 dtex were superior). Also, the ratio of the basis weight of the upper web to the basis weight of the lower web may have a value other than 1.2:1, though it preferably is in the range 1.1:1 to 2:1.

Figure 2:
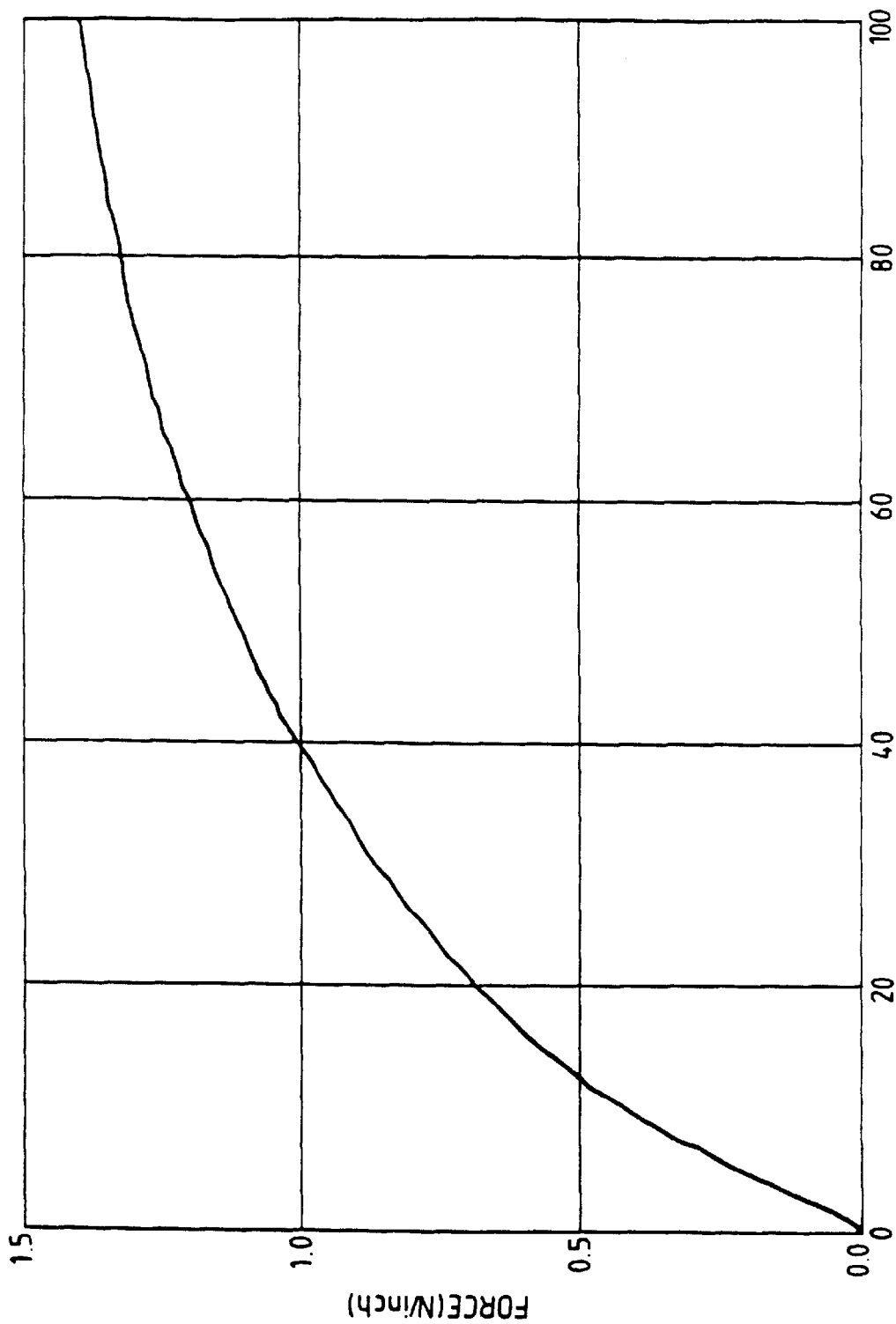
FIG. 2 is a stress-strain curve for an embodiment of topsheet according to the invention.
Figure 3:
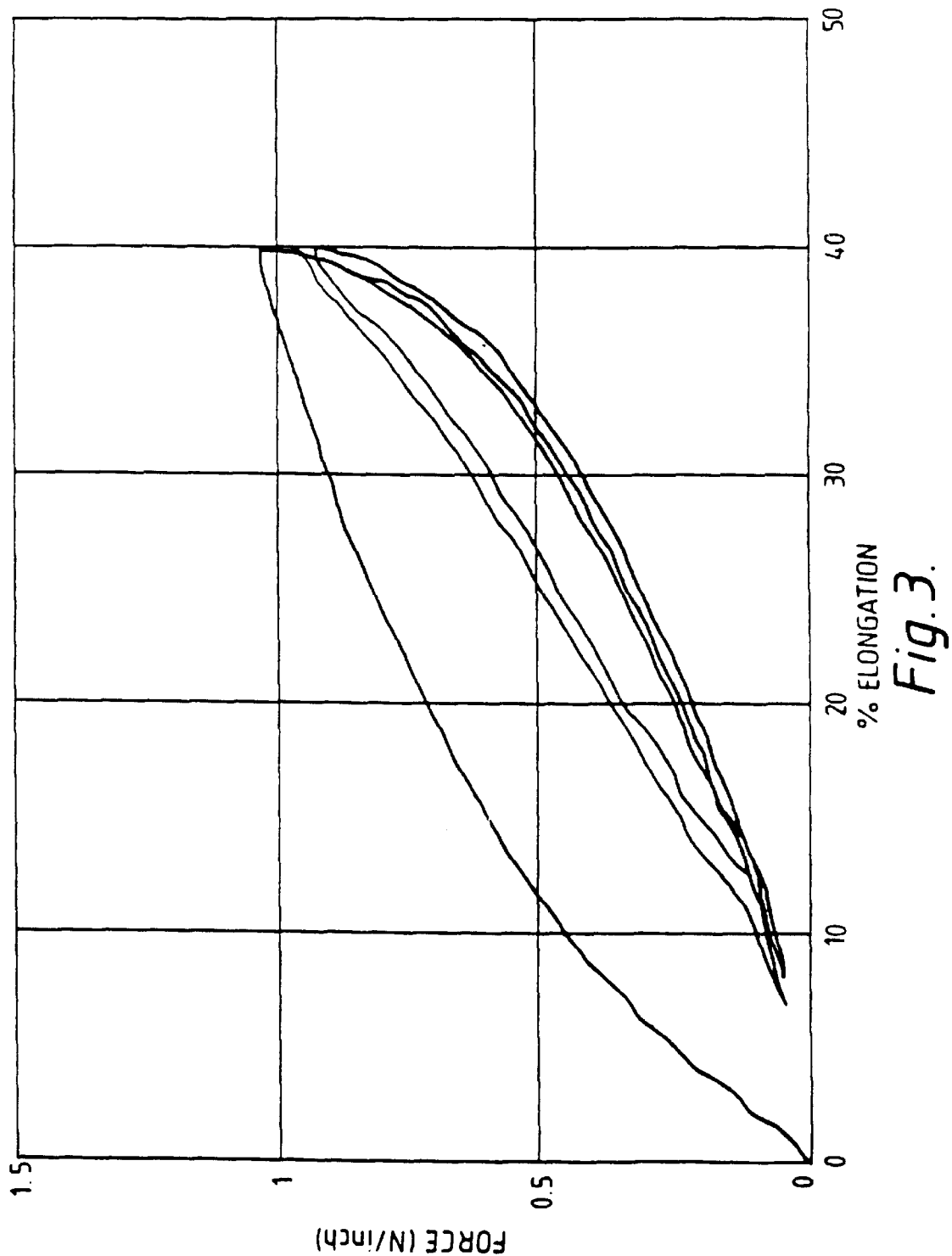
FIG. 3 is a hysteresis diagram for the embodiment topsheet to which FIG. 2 relates.
Figure 4:
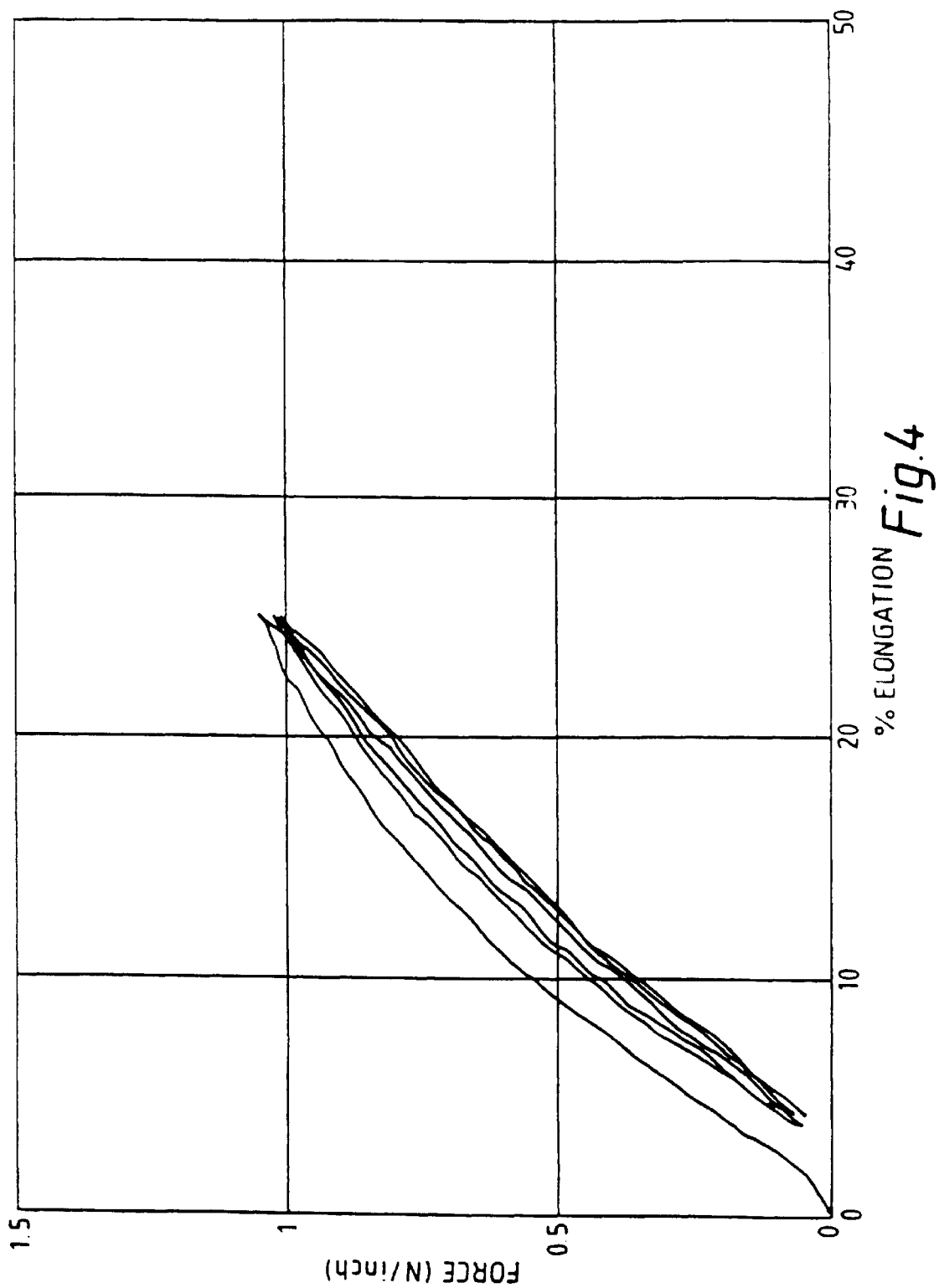
FIG. 4 is a hysteresis diagram for the elastic film used in that embodiment.

The graph shown in FIGS. 2 to 4 relate to the embodiment just described. FIG. 2 shows the percentage elongation achieved when a given force is applied to a rectangular sample of the material. The force is expressed as the force in N divided by the width of the sample, in inches, i.e. the distance transverse to the direction of application of the force. This shows that it was possible to elongate the material by an amount at least equal to its own length, without breaking it, and with the application of only a modest force.

FIG. 3 shows the result of carrying out a hysteresis test on a sample of the embodiment. This was stretched three times to elongate it by 40% each time, with the force being relaxed between each elongation to 0.05 N/inch. This graph shows that the force required to achieve 40% elongation varied very little from one elongation to the next, and that the amount of set (i.e. permanent elongation) produced by three elongations was less than 10%.

FIG. 4 shows the results of carrying out a test similar to FIG. 3, but on the elastic film itself. Comparison of FIGS. 3 and 4 shows that the elongation produced by a force of 1N/inch drops from about 40% to about 25% in going from the film by itself to the elastic product incorporating the film. This is a remarkably small drop bearing in mind that in the elastic product the elastic film is bonded to two quite substantial non-elastic webs.

The tests illustrated in FIGS. 2 to 4 were all carried out on samples 50 mm in length and 25.4 mm in width, and elongation was carried out at 100 mm/min.

Tests were carried out to compare the rewetting behaviour of two forms of coversheet according to the present invention (one with hydrophilic upper and lower webs, and the other with hydrophobic upper and lower webs) with the corresponding two forms of coversheet according EP-A-207904.

In all cases the fibres of the upper and lower webs were of polypropylene. The coversheet according to EP-A-207904 had a non-elastic central film of a polyolefin material. The results of the tests are given in the following table, which also gives the thickness of the samples under a pressure of 20 g/m².

| Rewetting | Thickness (under 20 g/m² pressure) | |
| --- | --- | --- |
| Hydrophilic Coverstock | 0.41 mm | 1.39 g |
| Hydrophilic Elasticated Coverstock | 0.37 mm | 1.02 g |
| Hydrophobic Coverstock | 0.41 mm | 0.03 g |
| Hydrophobic Elasticated Coverstock | 0.35 mm | 0.04 g |

The tests shows that the use of an elastic film as opposed to a non-elastic film has no significant effect on the rewetting behaviour of the coversheet.

Details of the method used for carrying out the rewetting test, and of the synthetic urine used in the test are given below.

Rewetting

The product is placed on an impermeable surface, and 2 ml of synthetic urine is introduced into the product, which is then left for 5 minutes. Five sheets of absorbent paper, each having a weight of 220 g/m² are placed over the product, and a weight which exerts a pressure of 5.9 kPa on the portion of the product under the weight is placed thereon. The weight is left in position for 15 seconds. The amount of liquid absorbed by the absorbent paper is taken as the rewetting value.

Synthetic urine

The synthetic urine used was a solution in distilled water of the following salts (in weight %): Urea 2%, sodium chloride 0.9%, magnesium sulfate (heptahydrate) 0.11%, calcium chloride (anhydrous) 0.06%.

What is claimed is:

1. A covering structure for covering an absorbent body of an absorbent sanitary article, the said structure having perforations which extend therethrough and being elastic in at least one direction, the structure comprising:

(a) an upper layer intended to face outwardly of the absorbent body and comprising a non-woven fibrous material;

(b) an intermediate layer comprising an elastic film; and (c) a lower layer intended to face inwardly towards the absorbent body and comprising a non-woven fibrous material; the upper and lower layers being connected to the intermediate layer substantially only around the perimeters of the perforations by at least partially-melted fibers of said non-woven fibrous material layers.

2. A structure according to claim 1, wherein at least one of the upper and lower layers is formed of carded fibres.

3. A structure according to claim 1, wherein at least one of the upper and lower layers comprises polypropylene fibres.

4. A structure according to claim 1, wherein at least one of the upper and lower layers comprises bicomponent fibres.

5. A structure according to claim 1, wherein at least one of the upper and lower layers is at least partly hydrophobic.

6. A structure according to claim 1, wherein at least one of the upper and lower layers is at least partly hydrophilic.

7. A structure according to claim 1, wherein the elastic film is based on a thermoplastic elastomer.

8. A structure according to claim 7, wherein the said elastomer is a styrenic block copolymer.

9. A structure according to claim 8, wherein the said copolymer is selected from the group consisting of styrene-butadiene-styrene, styrene-isoprene-styrene, styrene-ethylene butylene-styrene and styrene-ethylene propylene-styrene copolymers.

10. A structure according to claim 7, wherein the said elastomer is a polyurethane.

11. A structure according to claim 7, wherein the said elastomer is selected from the group consisting of polyesters, polyethers and copolymers thereof.

12. A structure according to claim 7, wherein the said elastomer is selected from the group consisting of polyester-amides and poly-ether-ester amides.

13. A structure according to claim 7, wherein the said elastomer is an ionomer.

14. A structure according to claim 7, wherein the said elastomer is a blend of ethylene vinyl acetate and a rubber.

15. A structure according to claim 7, wherein the said elastomer is a blend of a polyolefin and a rubber.

16. A structure according to claim 15, wherein the polyolefin is selected from the group consisting of polypropylene, linear low density polyethylene, and polyethylene/polypropylene copolymers.

17. A structure according to claim 1, wherein the elastic film has a thickness of not more than about 100 μm.

18. A structure according to claim 17, wherein the elastic film has a thickness of not more than about 70 μm.

19. A structure according to claim 18, wherein the elastic film has a thickness of from 30–50 μm.

20. A structure according to claim 18, wherein the elastic film has a thickness of from 15–30 μm.

21. An absorbent sanitary article provided with or covering structure on at least one face thereof, the said structure having perforations which extend therethrough and being elastic in at least one direction, the structure comprising:

(a) an upper layer intended to face outwardly of the absorbent body and comprising a non-woven fibrous material;

(b) an intermediate layer comprising an elastic film; and (c) a lower layer intended to face inwardly towards the absorbent body and comprising a non-woven fibrous material; the upper and lower layers being connected to the intermediate layer substantially only around perimeters of the perforations by at least partially-melted fibers of said non-woven fibrous material layers.

* * * * *